(12) United States Patent
Hausheer et al.

(10) Patent No.: US 6,468,963 B1
(45) Date of Patent: Oct. 22, 2002

(54) METHODS AND FORMULATIONS FOR REDUCING TOXICITY ASSOCIATED WITH DIABETES TREATMENTS

(75) Inventors: Frederick H. Hausheer, Boerne, TX (US); Aulma Parker, San Antonio, TX (US); Susan E. Hamilton, San Antonio, TX (US)

(73) Assignee: BioNumerik Pharmaceuticals, Inc., San Antonio, TX (US)

( * ) Notice: Subject to any disclaimer, the term of this patent is extended or adjusted under 35 U.S.C. 154(b) by 0 days.

(21) Appl. No.: 09/562,160

(22) Filed: May 1, 2000

(51) Int. Cl.$^7$ .................... A61K 31/155; A61K 31/185; A61K 31/662; A61K 38/26; A61K 38/28
(52) U.S. Cl. ................ 514/4; 514/12; 514/21; 514/108; 514/126; 514/127; 514/369; 514/563; 514/578; 514/592
(58) Field of Search .................. 514/3, 4, 12, 21, 514/108, 126, 127, 369, 553, 578, 592, 593, 635; 530/303, 304, 305

(56) References Cited

U.S. PATENT DOCUMENTS

| | | | | | |
|---|---|---|---|---|---|
| 4,927,762 | A | * | 5/1990 | Darfler | 435/240.31 |
| 6,031,006 | A | * | 2/2000 | Hausheer et al. | 514/711 |
| 6,043,274 | A | * | 3/2000 | Hausheer et al. | 514/517 |
| 6,075,053 | A | * | 6/2000 | Hausheer | 514/578 |
| 6,100,247 | A | * | 8/2000 | Hausheer et al. | 514/108 |
| 6,251,881 | B1 | * | 6/2001 | Hausheer et al. | 514/121 |
| 6,274,622 | B1 | * | 8/2001 | Hausheer et al. | 514/517 |

* cited by examiner

Primary Examiner—Jeffrey E. Russel
(74) Attorney, Agent, or Firm—Thomas J. Dodd

(57) ABSTRACT

Formulations and methods for reducing the unwanted toxicity and complications associated with treatments for diabetes mellitus. The formulations include co-formulations of an anti-diabetic agent and a toxicity reducing agent of the formula described in the specification. The methods include administration of effective amounts of the anti-diabetic agent and the toxicity reducing agent to safely treat the diabetic patient.

15 Claims, No Drawings

METHODS AND FORMULATIONS FOR REDUCING TOXICITY ASSOCIATED WITH DIABETES TREATMENTS

FIELD OF THE INVENTION

This invention relates to pharmaceutical formulations of a reducible disulfide compound and a diabetes treatment agent. The invention also includes a method of reducing the risks associated with the administration of anti-diabetes agents by administration of a reducible disulfide compound.

BACKGROUND OF THE INVENTION

Treatments for diabetes mellitus are dependent upon the type and severity of the disease in individual patients. Insulin is still the treatment of choice for type I diabetes, and is now often combined with an oral anti-diabetic agent to better provide control of the patient's blood sugar levels and reduce the risk of complications due to either dangerously high or low levels.

Type II diabetes mellitus is normally controlled with oral anti-diabetic agents, and if the disease worsens insulin may be employed for better control of the disease. Although insulin and most oral anti-diabetic agents are well tolerated by most patients, the risk of toxic reactions remains. Further, since diabetics usually administer their own medications and must remain on these medications for life, the risks are multiplied over the course of a number of years.

The main danger with insulin therapy is the risk of acute hypoglycemia and of subsequent diabetic rebound reactions, either of which can mitigate complications ranging from skin flushing to stroke and coma, even death.

Use of oral anti-diabetic agents can also result in acute hypoglycemia and rebound reactions, and these agents have also resulted in unwanted toxic effects such as GI disturbances, hepatotoxicity, skin rashes and other allergic reactions, hematologic toxicity and others. At times the adverse effects are serious enough to warrant a drop in dosage or discontinuance of the drug.

Mesna (sodium 2-mercaptoethane sulfonate) and dimesna (disodium 2,2'-dithiobis ethane sulfonate) are known therapeutic compounds, which have heretofore demonstrated a wide variety of therapeutic uses. Both mesna and dimesna have been shown to be effective protective agents against certain specific types of toxicity associated with the administration of cytotoxic drugs used to treat patients for various types of cancer.

In particular, mesna has been used in humans with some success in mitigating the toxic effects of certain antineoplastic alkylating agents such as if osfamide, cyclophosphamide, melphalane, trofosfamide, sulfosfamide, chlorambucil, busulfan, triaziquone, triethylene thiophosphamide, and others, as disclosed in U.S. Pat. No. 4,220,660, issued Sep. 2, 1980.

The near absence of toxicity of dimesna further underscores the usefulness of this compound, as large amounts can be given to a patient without increasing the risk of adverse effects from the protective agent itself.

Further, pharmacological profiles of each compound indicate that, if proper conditions are maintained, mesna and dimesna do not prematurely inactivate the main drug to any significant degree. Thus, neither compound will significantly reduce activity of the chemotherapeutic agent, and in many cases, act to potentiate the effect of the main drug on targeted cancer cells.

The structures of both mesna and dimesna are shown below.

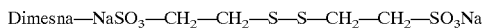

As shown, dimesna is a dimer of mesna, with the optimum conditions for oxidation occurring in the slightly basic (pH~7.3), oxygen rich environment found in blood plasma. In mildly acidic, low oxygen conditions, in the presence of a reducing agent such as glutathione reductase, conditions prevalent in the kidneys, the primary constituent is mesna.

Mesna and dimesna act as protective agents for a number of cytotoxic agents by substituting a nontoxic sulfhydryl moiety for a toxic hydroxy (or aquo) moiety. This action is particularly evidenced in the co-administration of mesna and an oxazaphosphorine, and in the administration of dimesna in conjunction with cisplatin and/or paclitaxel.

Mesna and dimesna, as well as most analogues of these compounds, have excellent toxicity profiles in mammalian species. Dimesna and other disulfide analogues have much better safety profiles than the mesna analogues having free thiol moieties. In fact, dimesna has been given to mice and dogs in doses higher than the accepted $LD_{50}$ for common table salt (3750 mg/kg), with no adverse effects. Dimesna has also been administered to humans in doses exceeding 40 $g/m^2$, with no adverse effects.

Mesna, and other analogues with free thiol moieties, constitute the more physiologically active form of the two types of compounds described in this specification. These compounds manifest their activity by providing free thiol moieties for terminal substitution at locations where a terminal leaving group of appropriate configuration is located.

Also, it is known that compounds with one or more free thiols tend to be highly water soluble, which means that their activity is generated mainly in the extracellular space. This significantly decreases drug-induced cell damage, which is common with other compounds of this general type that are more prone to pass through cell walls.

This profile is especially significant in explaining the success of dimesna in controlling and mitigating the toxic effects of platinum complex and taxane antitumor drugs. The mechanism for action in the case of cisplatin (cis-diammine dichloro platinum) is explained in U.S. Pat. No. 5,789,000, which is incorporated herein by reference.

Mesna, dimesna, and analogues of these compounds have been the subject of several prior pharmaceutical uses described in the literature and in prior patents, both in the United States and around the world. In addition to the cytotoxic agent protection uses, one or more of these compounds have proven effective, in vitro, against a multiplicity of biological targets, and have been effective, in vivo, in the treatment of sickle cell disease, radiation exposure, chemical agent exposure, and other uses.

Mesna, dimesna, and analogues thereof are synthesized from commonly available starting materials, using acceptable routes well known in the art. One such method involves the two-step, single pot synthetic process for making dimesna and like compounds of the following formula:

wherein:
  $R_1$ is hydrogen, X-lower alkyl, or X-lower alkylene-$R_3$;
  $R_2$ is -lower alkylene-$R_4$;
  $R_3$ and $R_4$ are each individually $SO_3M$ or $PO_3M_2$;
  X is absent or X is sulfur; and
  M is hydrogen or an alkali metal.

The process essentially involves a two-step single pot synthetic process, which results in the conversion of an alkenyl sulfonate salt or acid to the desired formula I compound. The process in the case of mesna is a single step process, which converts the alkenyl sulfonate salt to mesna or a mesna derivative by reacting with an alkali metal sulfide or with hydrogen sulfide.

If the desired end product is dimesna or a dimesna analogue, a two-step single pot process is involved. Step 1 is as described above. Step 2 of the process is performed in the same reaction vessel as Step 1 without the need to purify or isolate the mesna formed during that step. Step 2 includes the introduction of oxygen gas into the vessel, along with an increase in pressure and temperature above ambient values, at least 20 pounds per square inch (psi) and at least 60° C. Dimesna or a derivative thereof is formed in essentially quantitative yield.

Other processes, well known and documented in the prior art, may be employed to make either mesna or dimesna, or derivatives and analogues thereof.

SUMMARY OF THE INVENTION

The formulations and methods of this invention are employed to reduce the toxic effects and related complications associated with the administration of insulin and oral anti-diabetic agents used to treat patients with diabetes mellitus.

The compounds used in within the context of this invention are of the following formula I:

$$R_1\text{—}S\text{—}R_2; \tag{I}$$

wherein:

$R_1$ is hydrogen, X-lower alkyl, or X-lower alkylene-$R_3$;

$R_2$ is -lower alkylene-$R_4$;

$R_3$ and $R_4$ are each individually $SO_3M$ or $PO_3M_2$;

X is absent or X is sulfur; and

M is hydrogen or an alkali metal; or a pharmaceutically acceptable salt thereof.

Co-formulations according to this invention include a formula I compound mixed in the same formulation with insulin or an oral anti-diabetic agent. Co-formulations may be formulated for either parenteral administration (insulin co-formulations), or oral administration.

The invention also includes methods of reducing the unwanted toxicity associated with anti-diabetic agents, including all of the various forms of insulin. The methods involve the administration of effective amounts of the formula I compound in conjunction with the administration of the anti-diabetic agent, either in the same formulation or by separate dosage.

Accordingly, it is an object of this invention to provide for novel formulations and methods for safely treating patients with diabetes mellitus.

Another object is to provide for a method of reducing the toxicity and risks of associated complications in the treatment of diabetes mellitus.

Another object is to provide for a method of safely treating patients diagnosed with diabetes mellitus.

Other objects will become apparent upon a reading of the following description.

DESCRIPTION OF THE PREFERRED EMBODIMENTS

The preferred embodiments herein described are not intended to be exhaustive or to limit the invention to the precise forms disclosed. They are chosen and described to explain the principles of the invention, and the application and practical use thereof to best enable others skilled in the art to follow and implement its teachings.

For purposes of this invention, the following definitions apply:

"Lower alkyl" defines an aliphatic hydrocarbon of at least one and no more than six total carbon atoms. Likewise, "lower alkylene" refers to a bridge aliphatic hydrocarbon of from one to six total carbon atoms.

This invention includes pharmaceutical co-formulations of a compound of formula I, above, and an anti-diabetic agent used in the treatment of diabetes mellitus. The pharmaceutical co-formulations are preferably adapted for convenient administration via either parenteral or oral routes.

Preferred routes for administration normally will be the same as with single agent therapy, for convenience of use by the patient. Insulin and glucagon (which is an anti-hypoglycemic agent used to treat emergency hypoglycemic conditions) are injectable solutions while other available anti-diabetic agents are administered orally.

In parenteral formulations, the formula I compound is preferably dissolved or suspended in solution along with the insulin or glucagon peptide. Excipients, diluents, preservatives, etc. may be present in the formulation, as per the accepted practices for insulin and glucagon injectable solutions.

Co-formulations of insulin and the formula I compound include a standard concentration of insulin, usually 100 or 500 USP units per mL. As is well known, there are many different types of insulin available from various sources, as well as recombinant human and human analog insulins. The formula I compound is dissolved along with the insulin and stored in the same vial until administration. Concentrations of the formula I compound can vary, but are designed to deliver between 0.5 and 10 grams per dose.

Co-formulations of glucagon and the formula I compound are preferably dispensed in solid form and must be dissolved prior to injection. An effective dose of glucagon is typically considered to be 1 USP unit dissolved in 1 mL of sterile diluent. The formula compound is preferably supplied in co-formulation in lyophilized form and may be reconstituted in the diluent prior to injection. A preferred dose of formula I compound is between 40–200 mg.

Co-formulations of the formula I compound and oral anti-diabetic agents are preferably formulated in a swallowable form, such as tablets, gelatin capsules, etc. Most oral anti-diabetic agents are currently in tablet form, and co-formulations of these and the formula I compound preferably will retain that form for ease of administration.

Currently available oral anti-diabetic agent tablets range from 1 mg to 800 mg per dose. Some tablets are scored to allow the dose to be taken in two or more parts. Preferred co-formulations of the oral anti-diabetic agents and the formula I compound are combined in solid form in the same dosage form, with the preferred amount of the formula I compound ranging from 5 to 1000 times the amount of the anti-diabetic agent. Large excesses are preferred to ensure efficacy, since the formula I compounds are essentially non-toxic and do not interfere with the action of the primary drug.

The methods of this invention involve the administration of an effective amount of the formula I compound to a patient in combination with an anti-diabetic agent. The formula I compound may either be administered as a part of a co-formulation or in a separate formulation. Co-formulations are described above.

When describing the methods of this invention, the term effective amount refers to the amount of drug that produces a therapeutic response. In the case of the anti-diabetic agents, the effective amount is preferably that amount prescribed by the physician, which is effective in controlling the patient's blood sugar level and reduces the risk of complications. Standardized dosing schedules are available and well known for all of the available anti-diabetic agents, both injectables and oral treatments.

The term toxicity-reducing amount when referring to the formula I compound denotes the amount of formula I compound that can safely reduce the risks of toxicity of the anti-diabetic agent. Toxicity-reducing amounts are preferably expressed in terms of ratio of anti-diabetic agent to formula I compound. Preferably, the formula I compound is administered in a ratio between 3 and 3,000 times the amount of the anti-diabetic agent being administered.

Typically, the formula I compound is administered in large excess compared to the amount of the primary agent. This can occur because of the excellent safety profile of the formula I compounds and their almost total absence of unwanted toxicity. Further, since the formula I compounds do not deactivate the primary agents, large amounts can be administered without necessarily upping the dose of the primary drug.

The route of administration of the two agents can be tailored to suit the needs of the individual patient. Preferably in the case of oral anti-diabetic agents, the route of administration is also oral. Either the formula I compound may be formulated in the same swallowable carrier as the anti-diabetic agent, or it may be formulated separately.

If formulated in two distinct carriers, the formula I compound may be administered prior to, simultaneously with, or after the administration of the anti-diabetic agent. Preferably, the formula I compound is administered a short time before the anti-diabetic agent, between 5 minutes to 1 hour before administration of the anti-diabetic agent, most preferably between 15 and 30 minutes prior to administration.

The method takes into account that most anti-diabetic agents are self-administered. Slow release formulations of the formula I compound are also contemplated to ensure that sufficient concentrations remain in the patient's bloodstream when the anti-diabetic agent is administered.

Formulation technology regarding the anti-diabetic agents is well known in the art, and examples of formulations of the formula I compounds is disclosed in U.S. Pat. Nos. 5,789,000; 5,919,816; and others, which are incorporated herein by reference.

What is claimed is:

1. A pharmaceutical formulation adapted for administration to human patients, said pharmaceutical formulation comprising (a) an effective amount of an anti-diabetic agent; (b) an toxicity reducing amount of a agent of the formula:

$$R_1-S-R_2; \quad (I)$$

wherein:
  $R_1$ is hydrogen, X-lower alkyl, or X-lower alkylene-$R_3$;
  $R_2$ is -lower alkylene-$R_4$;
  $R_3$ and $R_4$ are each individually $SO_3M$ or $PO_3M_2$;
  X is absent or X is sulfur; and
  M is hydrogen or an alkali metal; or
  a pharmaceutically acceptable salt thereof; and
(c) one or more pharmaceutically acceptable solvents, excipients, diluents or preservatives.

2. The pharmaceutical formulation of claim 1 wherein the anti-diabetic agent is insulin or glucagon.

3. The pharmaceutical formulation of claim 1 wherein the anti-diabetic agent is a sulfonylurea.

4. The pharmaceutical formulation of claim 1 wherein the anti-diabetic agent is a biguanide or an α-glucosidase inhibitor.

5. The pharmaceutical formulation of claim 1 wherein the anti-diabetic agent is a thiazolidinone.

6. The pharmaceutical formulation of claim 1 wherein the anti-diabetic agent and the toxicity reducing agent are dissolved in a solution suitable for parenteral administration.

7. The pharmaceutical formulation of claim 3 wherein the anti-diabetic agent and the toxicity reducing agent are encapsulated in a swallowable carrier suitable for oral administration.

8. A method of reducing the unwanted toxicity of an agent administered to patients as a therapy for diabetes, said method comprising administering to the patient a toxicity reducing amount of the formula I compound of claim 1, within one hour prior to, simultaneously with, or after administration of the agent.

9. The method of claim 8 wherein the anti-diabetic agent is insulin or glucagon.

10. The method of claim 8 wherein the anti-diabetic agent is an oral anti-diabetic agent.

11. The method of claim 8 wherein the toxicity reducing amount of the formula I compound is from 3 to 3,000 times the amount of the anti-diabetic agent being administered.

12. The method of claim 9 or claim 10 wherein the formula I compound is administered orally.

13. The method of claim 9 or claim 10 wherein the formula I compound is administered parenterally.

14. The method of claim 8 wherein the formula I compound is administered in the same formulation with the anti-diabetic agent.

15. The method of claim 8 wherein the formula I compound is formulated separately from the anti-diabetic agent.

* * * * *